United States Patent [19]

Chen et al.

[11] Patent Number: 5,462,704
[45] Date of Patent: Oct. 31, 1995

[54] METHOD FOR PREPARING A POROUS POLYURETHANE VASCULAR GRAFT PROSTHESIS

[75] Inventors: Jui-Hsiang Chen, Hsinchu; Jeng Wei, Taipei; Andrew T. Hu, Hsinchu; Yu-Der Lee, Hsinchu; Ru-Fong Laiw, Hsinchu; Muh-Lan Chen, Hsinchu; Chung-Yi Chang; Fan-Yen Lee, both of Taipei; Shu-Fang Jiang, Hsinchu, all of Taiwan

[73] Assignee: Industrial Technology Research Institute, Hsinchu, Taiwan

[21] Appl. No.: 233,455

[22] Filed: Apr. 26, 1994

[51] Int. Cl.$^6$ .................................... B29C 67/20
[52] U.S. Cl. ............... 264/41; 264/233; 264/331.19; 264/343
[58] Field of Search .......... 264/41, 233, 331.19, 264/334, 343

[56] References Cited

U.S. PATENT DOCUMENTS 4,704,130  11/1987  Gilding et al. ................ 264/41 X

*Primary Examiner*—Leo B. Tentoni
*Attorney, Agent, or Firm*—Darby & Darby

[57] ABSTRACT

A porous polyurethane tube suitable for use as a vascular graft prosthesis is prepared by placing solvent type polyurethane resin coated mandrel in a static coagulant consisting of water, ethanol and optionally aprotic solvent within 30 seconds immediately after the coating step, separating the tube by placing the mandrel in a swelling agent containing at least 90 percent by weight of ethanol and rinsing with a solution containing at least 80 percent by weight ethanol.

12 Claims, 2 Drawing Sheets

METHOD FOR PREPARING A POROUS POLYURETHANE VASCULAR GRAFT PROSTHESIS

BACKGROUND

The present invention relates to a method for preparing porous polyurethane vascular graft prostheses, and in particular to a method for preparing porous polyurethane vascular grafts by placing polyurethane coated mandrel in a coagulant consisting of water, ethanol and optionally aprotic solvent.

Vascular graft prostheses have been used in clinical applications for many years to replace diseased arteries or, to act as shunting for blocked arteries, or to serve as graft fistula for blood dialysis.

Commercial available vascular graft prostheses include woven or knitted polyester fiber (Trademark Dacron) tubes and microporous expanded polytetrafluoroethylene (PTFE, tradename Teflon) tube, such as Gore-Tex(Gore & Associates, Inc.) or Impra Teflon(IMPRA, Inc.) vascular graft prostheses. When vascular graft prostheses made from Dacron or Teflon tubing have a relatively large diameter, good clinical results are obtained because the blood flow rate is high and therefore does not lead to thrombus formation on the luminal surface therein. However, when the Dacron or Teflon tubings have a relatively small diameter, the clinical performance are unsatisfactory because the blood flow rate is usually slow and therefore causes thrombus.

In view of the above mentioned drawbacks to vascular graft prostheses made from Dacron or Teflon, vascular graft prostheses made from polyurethane material have already been developed and have proven to be suitable for this purpose because they possess good blood compatibility.

For example, David Annis, Thien V. How and A. C. Fisher disclose a porous polyurethane vascular graft which is prepared by an electrostatic spinning and winding method. The method includes extruding polyurethane resin "Biomer" (tradename, Ethicon, Inc.) through a spinneret to form filaments and winding the filaments on a rotating mandrel by electrostatic force to form a porous polyurethane tubing having an internal diameter of 10mm ("A compliant small diameter arterial prosthesis," CRC press, 1987; "The design of a small diameter arterial replacement," in *Polymers in medicine: Biomedical and pharmacological applications* Emo Chiellini & Paolo Giusti Eds, Plenum Press, 1983; "Recent Advances in the development of artificial devices to replace diseased arteries in man: A new elastomeric synthetic artery graft," in *Polyurethanes in Biomedical Engineering*, Elsevier Science Publishers, 1984; " The design of a small diameter arterial replacement, in *Polymers in medicine: Biomedical and Pharmacological Applications* Emo Chiellini & Paolo Giusti Eds, Plenum Press, 1983).

The exact components of the above-mentioned "Biomer" polyurethane resins are not known, however, according to Michael D. Lelah, such resins are solvent type polyurethanes synthesized from polytetramethylene glycols having a molecular weight of 2000, 4,4'-diphenylmethanee diisocyanate(MDI), mixture of diamines and silicon compounds (*Polyurethane in medicine*, CRC press, Inc. 1986).

S. Gogolewski and A. J. Pennings disclose a biodegradable vascular graft prosthesis having an internal diameter of 10 mm and an average pore size of 40–50 μm. The biodegradable vascular graft is prepared by dipping a fluorizated stainless steel mandrel in a mixed resin of a polyurethane resin dissolved in a mixed solvent of DMF and THF and a polyacetide resin dissolved in DMF solvent, followed by placing the coated mandrel in a coagulant consisting of ethanol and water (volume ratio=1:1) ("Compliant, Biodegradable vascular prosthesis" in *Polyurethanes in biomedical engineering*, Elsevier Science Publishers, 1984).

J. G. F. Bots, L. Van der Does, A. Bantjes disclose a blood vessel prosthesis having pore size of 5–200 μm, which is prepared by forming filaments from a solution of polyethylene oxide, polypropylene oxide and dicumylperoxide, followed by winding the filaments on a rotating mandrel and irradiating them with UV light for 60 minutes. The solvents for dissolving the resins are a mixture solvent of dichloromethane and dichloroethane ("Small diameter blood vessel prostheses from polyethers," in *Polymers in medicine II*, edited by E. chielline, et al, 1986).

Thomas E. Brothers, James C. Stanley, William e. Burkel and Linda M. Graham disclose a vascular graft. The method for preparing the vascular graft includes forming a polyurethane tubing from a PU resin, B. F. Goodrich Estane 5714 (tradename) to which are added salts, by using the principle of phase inversion, and extracting the salts from the PU resin. The detailed manufacturing procedures are not disclosed ("Small caliber polyurethane and polytetrafluoroethylene grafts: A comparative study in a canine aortoiliac model" *Journal of Biomedical Materials Research*, vol. 24, pp 761–771, 1990).

Rajagopal R. Kowligi, Wolf W. Von Maltzahn and Robert C. Eberhart disclose a polyurethane tubing fabricated by using the precipitation-flotation method. The method includes premixing polyurethane resin with nitrogen gas in a spray nozzle, spraying the premixture on a flowing water bath in which a rotating mandrel is immersed, causing the polyurethane resin to form into filaments and to coagulate on the water bath and be taken up by the mandrel to form a porous polyurethane tubing. The polyurethane material used is a polyurethane resin with a tradename, "Surethane" and a solid content of 2–5%. The exact components of the polyurethane resin is not disclosed ("Synthetic vascular graft fabrication by a precipitation-floation method," *Trans Am Soc Artif Intern Organs*, Vol. XXX IV, pp 800–803(1988)).

White et al disclose a microporous polyurethane vascular graft prepared by using replamineform method. The method includes coating a reactive liquid polyurethane resin over a cylindrical mandrel which is formed by mechanically polishing a needlelike protrusion of sea urchin having the composition of calcite, carrying out the polymerization in situ and dipping the mandrel together with the polyurethane tubing formed thereon in a hydrochloride solution to dissolve the mandrel. The resultant polyurethane tubing has an average pore size of 15–20 μm(Michael d. Lelah,"Polyurethane in Medicine", CRC Press, Inc 1986)

Lyman et al also disclose a method of fabricating polyurethane tubing. Their method uses polyurethane resin synthesized from MDI and polypropylene oxide having a molecular weight of 1078 and ethylene diamine. The polyurethane tubing is obtained by using repeated dipping and precipitation method. The precipitating solution used is consisted of water and Dimethyl Formamide(DMF)(Michael d. Lelah, "Polyurethane in Medicine", CRC Press, Inc. 1986) , Leidner et al also disclose a method of fabricating porous polyurethane tubings. The method for this fabrication includes extruding polyurethane solution or melt into filaments, stretching the filaments and winding on a rotating mandrel to form a porous tubing(Michael d. Lelah,"*Polyurethane in Medicine*", *CRC Press, Inc* 1986)

Kozaburo Hayaski, Tomoyuki Saito et al synthesized a polyurethane resin by using MDI, polytetramethylene glycol(PTMG), polyethylene oxide-polydimethylsiloxanepolyethylene oxide(PES) and ethylene glycol as raw material and reported that a porous polyurethane vascular graft was fabricated. However, the actual procedures and conditions for this fabrication have not been disclosed ("Elastic properties and strength of a novel small-diameter, compliant polyurethane vascular graft," J. Biomed, Mater Res: *Applied Biomaterials*, vol 123, No. A2, p229–244, 1989).

Shu Qin Lin and Makoto Kodama et al used an aliphatic polyurethane resin, tradename, Tecoflex Sc 80A, having a solid content of 5–10% and solvent 1,4-dioxane, to produce porous polyurethane vascular prostheses. The polyurethane resin is injected into a cavity of a mold, frozen at a temperature of 0° to −196° C. and thawed to obtain a porous polyurethane vascular prosthesis with a pore size form several μm to 70 μm ("Porous polyurethane vascular prostheses with variable compliances", *Journal of Biomedical Materials Research*, Vol. 26, 1489–1502(1992)).

SUMMARY OF THE INVENTION

The object of the invention is to provide a method for producing a vascular graft prosthesis made of porous polyurethane polymer tubing which has superior biocompatability, in particular, blood compatability and uniform porous structure.

The object is achieved by providing a method including the steps of coating a solvent type polyurethane resin over the outer surface of a cylindrical mandrel; within 30 seconds immediately after the coating, placing the coated mandrel in a static coagulant having a temperature of 15°–40° C. for 2 to 12 hours to form a porous polyurethane tubing surrounding the mandrel, and followed by placing the mandrel surrounded with the porous polyurethane tubing in a swelling agent for 5 to 60 minutes. The solvent type polyurethane resin, according to the present invention, is prepared from polytetramethylene glycol, glycols and 4,4'-diphenylmethane diisocyanate, and has a solid content of 15–45 percent by weight and a viscosity of 10,000 to 150,000 centipoises.

The solvent type polyurethane resin is prepared from 1 mole of polytetra-methylene glycol, from 0.8 to 4 moles of glycol, and from 1.8 to 5 moles of 4,4'-diphenylethane diisocyanate. The coagulant according to the invention consists of water, ethanol and optionally an aprotic solvent. The aprotic solvent is N,N-dimethyl formamide(DMF) or N,N-dimethyl acetamide(DMAc). The swelling agent according to the invention should include at least 90 percent by weight of ethanol. The swelled porous polyurethane tubing, after being removed from the mandrel, is rinsed with a solution containing at least 80 percent by weight of ethanol for 5 to 120 minutes, and then dried.

According to an aspect of the method of the invention, in order to obtain porous vascular graft prosthesis with uniform porous structure, it is important that the coagulant consists of 10 to 50 percent by weight water and 90 to 50 percent by weight solvent selected from ethanol and aprotic solvent. The weight fraction of the ethanol is between 1.0 and 0.4 and the weight fraction of the aprotic solvent is between 0 and 0.6.

BRIEF DESCRIPTION OF THE DRAWINGS

The present invention can be more fully understood by reference to the following detailed description and accompanying drawings, which form an integral part of this application.

DETAILED DESCRIPTION OF THE INVENTION

According to the method of the invention, the solvent type polyurethane resin is prepared by solution polymerization, i.e. polymerizing the necessary ingredients for the synthesis of polyurethane, that is, diisocyanate, chain extender and long chain polyol in an aprotic solvent, for example N, N-dimethyl formamide or N,N-dimethyl acetamide. Either one-shot process or prepolymer process can be used. It is essential for the method of the invention that the diisocyanate is an aromatic diisocyanate, i.e. 4,4'-diphenylmethane diisocyanate (MDI), because MDI has good reactivity, and therefore in synthesizing polyurethane, it is not necessary to add any catalyst to facilitate the polymerization reaction. If an aliphatic diisocyanate is used, organic metals or amine must be added as a catalyst which remains in the fabricated polyurethane product after the polymerization, causing cytotoxicity problems when the polyurethane polymer is used as the material for vascular graft prosthesis. Another advantage of using MDI is that the synthsized polyurethane polymers demonstrate superior mechanical strength, and therefore are able to provide a tough vascular graft prosthesis so as to reduce the possibility of distoration of the vascular graft prosthesis after they have been implanted in human body.

The chain extenders suitable for use in the method of the invention are short chain glycols. Examples of these short chain glycols are ethylene glycol, 1,4-butylene glycol and 1,6-hexamethylene glycol. The advantage of using short chain glycols as the chain extender is that homogeneity of the final product can be obtained. If diamines are used as chain extender in the solution polymerization of polyurethane, nonhomogeneity of the final product results because the polymerization normaly proceeds too quickly and a crosslinking side reaction occurs. Using short chain glycols can eliminate this drawback.

The long chain polyols suitable for use according to the method of the invention include various polyesters, polyethylene oxides, polypropylene oxides, polycaprolactons, polysulfides, polysilicone and polytetramethylene glycols. Among these, polytetramethylene glycol is preferred because it has superior mechanical properties, hydrolysis resistance and biocompatibility and blood compatibility.

It is also important to the method of the invention that the solid content and viscosity of the resultant polyurethane resin should be controlled in a specific range so that the polyurethane resin can be uniformly coated over the outer surface of a cylindrical mandrel. The resultant polyurethane resin should have a solid content of 15 to 45 percent by weight and a viscosity of 10,000 to 150,000 centipoises when measured by a Brookfield viscosimeter at room temperature (25° C.). The cylindrical mandrel is preferably a metal mandrel with an outer diameter of 2 mm to 15 mm. In addition, according to the present invention, the coating of polyurethane resin over the mandrel should be conducted at a temperature of 10° to 40° C.

According to the invention, the coating is conducted by dropping the mandrel to be coated through a vertically mounted cylindrical container which is filled with the polyurethane resin, from its top open end to its bottom. A hole having a size suitable for the passing of the mandrel is formed at the bottom of the cylindrical container and positioning screws are provided at lower part of the container to ensure the passing of the mandrel through the hole. After the coating, the coated mandrel is placed in a coagulant to form a porous polyurethane tubing surrounding the mandrel. Note that the coated mandrel should be placed in the coagulant within 30 seconds immediately after the coating and the coagulant should be in a static state when the mandrel is placed in. According to the invention, a vessel containing coagulant is mounted below the coating cylinder so that the coated mandrel can be directly and quickly dropped into the coagulant within 30 seconds.

The coagulant suitable for use in the present invention consists of water, ethanol and optionally, an aprotic solvent, for example N,N-dimethyl formamide or N,N-dimethyl acetamide. In order to obtain a porous polyurethane tubing, the fraction of the ingredients of the coagulant must be properly controlled. The amount of each ingredients of the coagulant should be accorded with the following two equations:

$$W+(100-W)(ESF+ASF)=100(\%)$$

$$ESF+ASF=1$$

wherein

W=wt % of water (nonsolvent) in coagulant

ESF=weight fraction of ethanol solvent based on the total solvent used in the coagulant ASF=weight fraction of aprotic solvent on the total solvent used in coagulant, $$ESF = \frac{\text{weight of ethanol}}{\text{weight of ethanol + weight of aprotic solvent}}$$

and $$ASF = \frac{\text{weight of apartic solvent}}{\text{weight of ethanol + weight of aprotic solvent}}$$

It has been found that in order to obtain a polyurethane tubing with a uniform distribution of pore size and without large cavities formed on the tubing wall, the parameter W should be in the range of 10–50, S should be in the range of 90 to 50, ESF should be in the range of 1.0 to 0.4 and ASF should be in the range of 0 to 0.6.

The coated mandrel is placed in the above-mentioned coagulant for a period of 2 to 12 hours according to the method of the invention. The coagulant should be maintained at a temperature of from 15° C. to 40° C.

The porous polyurethane tubings are separated from the mandrels by first placing the mandrel surrounded with the porous polyurethane tubing in a swelling agent to swell the polyurethane tubing and then removing the porous polyurethane tubings from the mandrel. The swelling agent suitable for use in the method of the invention should contain at least 90 percent by weight ethanol. A swelling agent consisting of 90 percent by weight ethanol and 10 percent by weight water is preferred for use in the invention. To facilitate the separation, the mandrel is placed in the swelling agent for 5 to 60 minutes.

The separated polyurethane tubings are then rinsed with a solution. The rinsing should last for 5 to 130 minutes to remove any possible PU oligomer remaining thereon. The solution for this purpose should contain at least 80 percent by weight ethanol. An aqueous solution contains 80 percent by weight ethanol and 20 percent by weight water is preferred for use according to the method of the invention.

After drying at, for example 20°–50° C., the porous polyurethane vascular grafts of the invention are obtained. The drying can be conducted by any method known to those skilled in this art.

This invention is more specifically described by the following illustrative examples.

Example 1

Synthesis of the solvent type polyurethane resins

In this example, solvent type polyurethane resins No. 1–16 of Table 1 below were prepared by one-shot process or prepolymer process. For one-shot process, polytetramethylene glycols, glycols, 4,4'-diphenylmethane diisocyanates in an amount as specified in Table 1, and suitable amount of aprotic solvents, were fed into a reactor, stirred and allowed to polymerize at a temperature of 70°–75° C. When the viscosity of the polyurethane reached the specific value as respectively indicated in Table 1, NCO terminators were added to the polymerization system to terminate the reaction. For prepolymer process, theoretical amount of polytetramethylene glycols(PTMG), 4,4'-dimethylmethane diisocyanates(MDI) and suitable amount of aprotic solvents were added to a reactor first to react to a prepolymer with NCO groups at its terminals, then chain extender, i.e. short-chain glycols, were added to allow the viscosity to increase to the specific value, and followed by adding NCO terminators to terminate the polymerization reaction.

TABLE 1

| PU resin No. | PTMG:Glycol:MDI (mole ratio) | Solid content (%) | Viscosity ($\times 10^{-3}$ cps) | Polymerization method | Aprotic solvent |
|---|---|---|---|---|---|
| 1 | PTMG (Mw = 1000) PTMG:BG:MDI 1:3:4 | 30 | 8.0 | one-shot | DMF |
| 2 | PTMG (Mw = 1000) PTMG:BG:MDI 1:2:3 | 30 | 12.8 | one-shot | DMF |
| 3 | PTMG (Mw = 1000) PTMG:BG:MDI 1:1.5:2.5 | 30 | 10.6 | one-shot | DMF |
| 4 | PTMG (Mw = 1000) PTMG:BG:MDI 1:1.2:2.2 | 30 | 8.8 | one-shot | DMF |
| 5 | PTMG (Mw = 1000) PTMG:BG:MDI 1:1:2 | 30 | 6.7 | one-shot | DMF |
| 6 | PTMG (Mw = 1000) PTMG:BG:MDI 1:0.8:1.8 | 30 | 5.1 | one-shot | DMF |
| 7 | PTMG (Mw = 1000) PTMG:BG:MDI 1:1:2 | 45 | 16.0 | one-shot | DMAc |
| 8 | PTMG (Mw = 1000) PTMG:BG:MDI 1:1:2 | 30 | 13.2 | prepolyner | DMF |
| 9 | PTMG (Mw = 1000) PTMG:EG:MDI 1:1:2 | 30 | 12.0 | prepolyner | DMF |
| 10 | PTMG (Mw = 1000) PTMG:HG:MDI 1:1:2 | 30 | 18.2 | prepolymer | DMF |
| 11 | PTMG (Mw = 2000) PTMG:BG:MDI 1:4:5 | 30 | 7.6 | one-shot | DMF |
| 12 | PTMG (Mw = 2000) PTMG:BG:MDI 1:3:4 | 30 | 7.2 | one-shot | DMF |
| 13 | PTMG (Mw = 2000) PTMG:BG:MDI 1:2.7:3.7 | 30 | 8.2 | one-shot | DMF |
| 14 | PTMG (Mw = 2000) PTMG:BG:MDI 1:2:3 | 30 | 6.0 | one-shot | DMF |
| 15 | PTMG (Mw = 2000) PTMG:BG:MDI 1:1:2 | 30 | 2.1 | one-shot | DMF |
| 16 | PTMG (Mw = 2000) PTMG:BG:MDI 1:1:2 | 15 | 4.6 | one-shot | DMAc |

Note:
BG = Butylene Glycol
EG = Ethylene Glycol
HG = Hexamethylene Glycol
PTMG = polytetramethylene glycol
MDI = 4,4'-Diphenylmethane diisocyanate
DMF = N,N-Dimethyl Formamide
DMAc = N,N-Dimethyl Acetamide

Example 2

Polyurethane resin No. 1 of Table 1 was coated over the outer surfaces of a cylindrical metal mandrel having an outer diameter of 8 mm with a thickness of 0.5 mm. Within 30 seconds immediately after the coating, the coated mandrels were placed in static coagulants having the components as set forth in Table 2.1. Porous polyurethane tubings 1WA 100-0705, 1WA9010-0705, 1WA8020-0705, 1WA7030-0705, and 1WA6040-0705 were prepared by following the procedures of the invention and the conditions as indicated in Table 2.1.

Figure 1A:
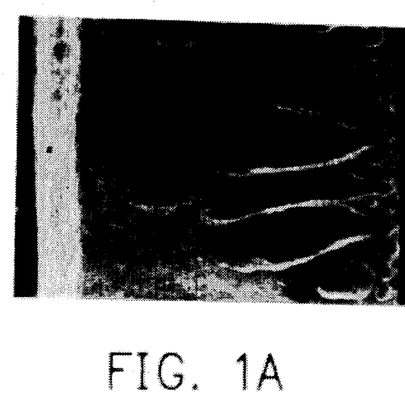
FIG. 1A is a scanning electron microphotograph of a cross-section of the wall of the porous polyurethane tubing 1WA100-0705, showing the morphology of the pore distribution.
Figure 1B:
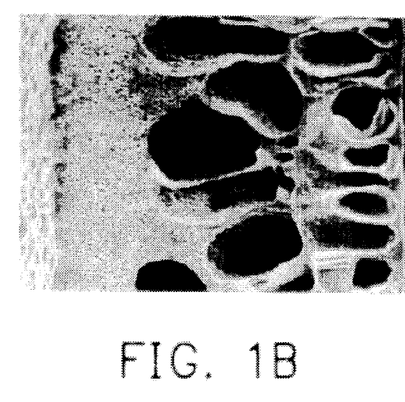
FIG. 1B is a scanning electron microphotograph of a cross-section of the wall of the porous polyurethane tubing 1WA9010-0705, showing the morphology of the pore distribution.
Figure 1C:
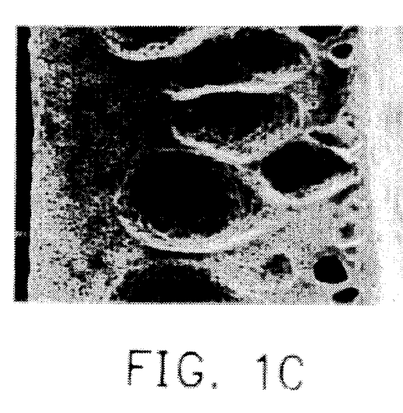
FIG. 1C is a scanning electron microphotograph of a cross-section of the wall of the porous polyurethane tubing 1WA8020-0705, showing the morphology of the pore distribution.
Figure 1D:
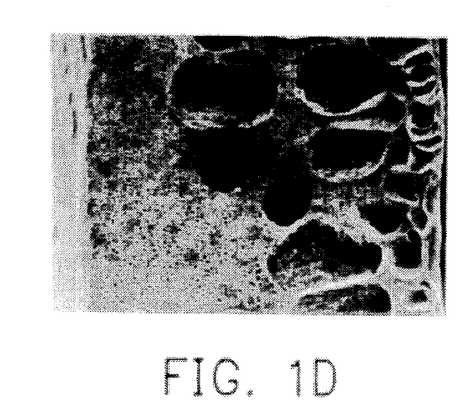
FIG. 1D is a scanning electron microphotographs of a cross-section of the wall of the porous polyurethane tubing 1WA7030-0705, showing the morphology of the pore distribution.
Figure 1E:
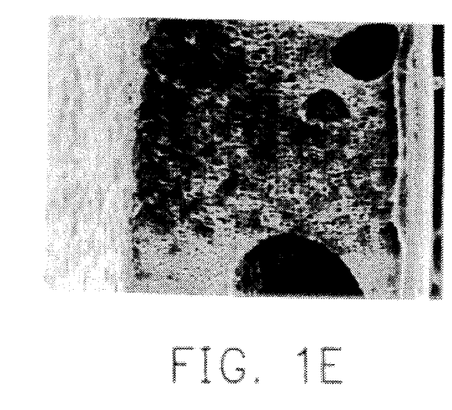
FIG. 1E is a scanning electron microphotographs of a cross-section of the wall of the porous polyurethane tubing 1WA6040-0705, showing the morphology of the pore distribution.

Certain physical properties of these prepared tubings are summarized in Table 2.2. Scanning electron microphotographs of the porous polyurethane tubings of the invention are shown in FIGS. 1A–1E. It can be seen from Table 2.2 that the burst pressure of the porous polyurethane tubings of the invention in every case exceeds 2280 mmHg, indicating that the blood pressure that the porous polyurethane tubings of the invention can endure is about 19 times that of the physiologic systolic pressure, if normal average human physiologic systolic pressure is considered to be 120 mm Hg. In addition, the cytotoxicities and hemolytic indexes as set forth in Table 2.2 indicate that the porous polyurethane tubings of this example show no cytotoxicity response or hemolytic phenomenon, and therefore can be used as vascular graft prostheses with superior results.

TABLE No. 2.1

| Coagulant No. | WA 100 | WA 9010 | WA 8020 | WA 7030 | WA 6040 |
|---|---|---|---|---|---|
| Composition of Coagulant (Water/DMF, wt/wt %) | 100/0 | 90/10 | 80/20 | 70/30 | 60/40 |
| Temperature of Coagulant (°C.) | 25 ± 2 | 25 ± 2 | 25 ± 2 | 25 ± 2 | 25 ± 2 |
| Coagulating Time (hour) | 6 | 6 | 6 | 6 | 6 |
| Composition of Swelling Agent (Water/Ethanol, wt/wt %) | 10/90 | 10/90 | 10/90 | 10/90 | 10/90 |
| Temperature of Swelling Agent (°C.) | 25 ± 2 | 25 ± 2 | 25 ± 2 | 25 ± 2 | 25 ± 2 |
| Swelling Time (min) | 10 | 10 | 10 | 10 | 10 |
| Composition of Rinsing Solution (Water/Ethanol, wt/wt %) | 20/80 | 20/80 | 20/80 | 20/80 | 20/80 |
| Rinsing Time (min) | 30 | 30 | 30 | 30 | 30 |
| Drying Temperature (°C.) | 40 ± 2 | 40 ± 2 | 40 ± 2 | 40 ± 2 | 40 ± 2 |
| Porous PU tubing No. | 1WA100-0705 | 1WA9010-0705 | 1WA8020-0705 | 1WA7030-0705 | 1WA6040-0705 |

TABLE 2.2

| | Porous PU tubing | | | | |
|---|---|---|---|---|---|
| PU Tubing Characteristics | 1WA100-0705 | 1WA9010-0705 | 1WA8020-0705 | 1WA7030-0705 | 1WA6040-0705 |
| Internal Diameter (mm) | 7.5 ± 0.2 | 7.5 ± 0.2 | 7.5 ± 0.2 | 7.4 ± 0.2 | 7.4 ± 0.2 |
| Wall Thickness (mm) | 0.48 ± 0.03 | 0.48 ± 0.03 | 0.48 ± 0.03 | 0.44 ± 0.03 | 0.42 ± 0.03 |
| Pore Homogeneity [1] | non-homogenous | non-homogenous | non-homogenous | non-homogenous | non-homogenous |
| Burst Pressure (mmHg) [2] | 2280 ± 76 | 2295 ± 76 | 2356 ± 76 | 2320 ± 76 | 2508 ± 76 |
| ASTM F895 Cytotoxicity [3] | 0/0 | 0/0 | 0/0 | 0/0 | 0/0 |
| Hemolytic Index % [4] | O | O | O | O | O |

Note:
(1) Pore homogeneity is determined by observing the pores distribution in wall-thickness direction by using a scanning electron microscope.
(2) Burst pressure is measured by increasing the internal pressure of the polyurethane tubing specimen with its one end sealed until tubing bursts. The final pressure at which the burst occurs is the burst pressure.
(3) Cytotoxicity is measured by the method described in ASTM F895 Standard Test for agar diffusion cell culture or cytotoxicity, and is represented by the Zone index/Lysis index. A result of 0/0 indicates that the test specimen shows no cytotoxicity response.
(4) Hemolytic index is an index of the degree of hemolysis caused by contacting the test specimen with blood. The hemolytic index is measured by the method described in the ASTM F756 "Standard practice for assessment of hemolytic properties for materials." A result of 0% indicates no hemolysis occurs.

Example 3

Polyurethane resin No. 2 of Table 1 was coated over the outer surfaces of cylindrical metal mandrels having an outer diameter of 13 mm and thickness of 1.2 mm. Within 30 seconds immediately after the coating, the coated mandrels were placed in static coagulants having the components as set forth in Table 3.1. Porous polyurethane tubings 2WE9010-1211, 2WE7030-1211, 2WE5050-1211, and 2WE3070-1211 were prepared by following the procedures of the invention and the conditions as indicated in Table 3.1.

Figure 2A:
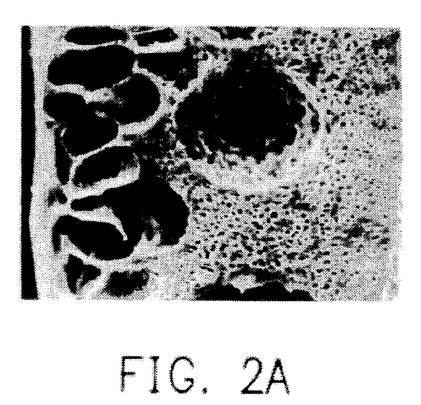
FIG. 2A is a scanning electron microphotographs of a cross-section of the wall of the porous polyurethane tubing 2WE9010-1211, showing the morphology of the pore distribution.
Figure 2B:
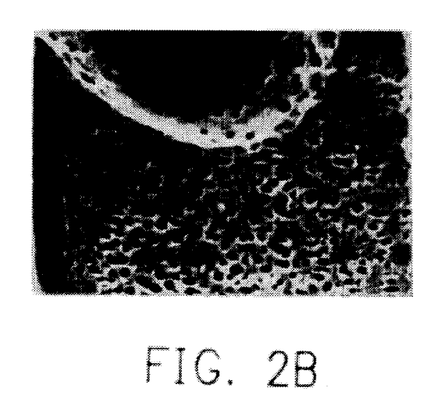
FIG. 2B is a scanning electron microphotographs of a cross-section of the wall of the porous polyurethane tubing 2WE7030-1211, showing the morphology of the pore distribution.
Figure 2C:
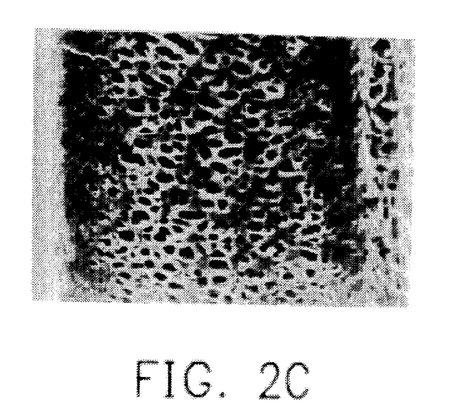
FIG. 2C is a scanning electron microphotographs of a cross-section of the wall of the porous polyurethane tubing 2WE5050-1211, showing the morphology of the pore distribution.
Figure 2D:
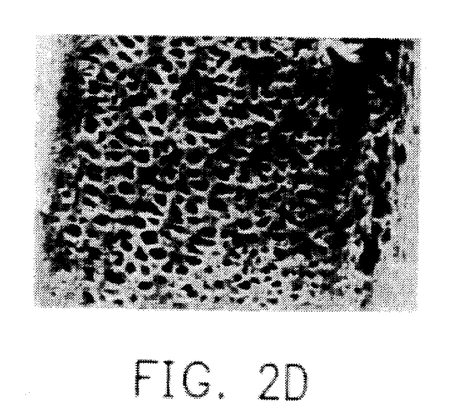
FIG. 2D is a scanning electron microphotographs of a cross-section of the wall of the porous polyurethane tubing 2WE3070-1211, showing the morphology of the pore distribution.

Certain physical properties of these prepared tubings are summarized in Table 3.2. Scanning electron microphotographs of the porous polyurethane tubings of the invention are shown in FIGS. 2A–2D. As shown in these photographs, porous polyurethane tubings having uniform porous structure can be obtained when water/ethanol solution is used as the coagulant, and the amount of the weak solvent, i.e. the ethanol, exceeds 50 wt %. Also it can be seen from Table 3.2 that the burst pressure of the porous polyurethane tubings of the invention in every case exceeds 2350 mmHg, indicating that the blood pressure that the porous polyurethane tubings of the invention can endure is about 20 times that of the systolic pressure, if normal average human systolic pressure is considered to be 120mm Hg. In addition, the cytotoxicity and hemolytic indexes as set forth in Table 3.2 indicate that the porous polyurethane tubings of this example show no cytotoxicity response or hemolytic phenomenon, and therefore can be used as vascular graft prostheses with superior results.

TABLE 3

| | Porous PU Tubing | | | |
|---|---|---|---|---|
| PU Tubing Characteristics | 2WE9010-1211 | 2WE7030-1211 | 2WE5050-1211 | 2WE3070-1211 |
| Internal Diameter (mm) | 12.0 ± 0.2 | 12.0 ± 0.2 | 12.0 ± 0.2 | 11.8 ± 0.2 |
| Wall Thickness (mm) | 1.13 ± 0.05 | 1.13 ± 0.05 | 1.13 ± 0.05 | 1.10 ± 0.02 |
| Pore Homogeneity | non-homogenous | non-homogenous | homogenous | homogenous |
| Brust Pressure (mmHg) | — | 2350 ± 76 | 2660 ± 76 | 2710 ± 76 |
| ASTM F895 Cytotoxicity | 0/0 | 0/0 | 0/0 | 0/0 |
| ASTM F756 Hemolytic Index (%) | O | O | O | O |

TABLE 3.1

| Coagulant No. | WE9010 | WE7030 | WE5050 | WE3070 |
|---|---|---|---|---|
| Composition of Coagulant (Water/Ethanol, wt/wt %) | 90/10 | 70/30 | 50/50 | 30/70 |
| Temperature of Coagulant (°C.) | 20 ± 2 | 20 ± 2 | 20 ± 2 | 20 ± 2 |
| Coagulating Time (hour) | 4 | 4 | 4 | 4 |
| Composition of Swelling Agent (Water/Ethanol, wt/wt % | 5/95 | 5/95 | 5/95 | 5/95 |
| Temperature of Swelling Agent (°C.) | 30 ± 2 | 30 ± 2 | 30 ± 2 | 30 ± 2 |
| Swelling Time (min) | 5 | 5 | 5 | 5 |
| Composition of Rinsing Solution (Water/Ethanol, wt/wt %) | 15/85 | 15/85 | 15/85 | 15/85 |
| Rinsing Time (min) | 5 | 5 | 5 | 5 |
| Drying Temperature (°C.) | 30 ± 2 | 30 ± 2 | 30 ± 2 | 30 ± 2 |
| Porous PU tubing No. | 2WE9010-1211 | 2WE7030-1211 | 2WE5050-1211 | 2WE3070-1211 |

Example 4

Polyurethane resin No. 3 of Table 1 was coated over the outer surfaces of cylindrical metal mandrels having an outer diameter of 6 mm and a coating thickness of 1.1 mm. Within 30 seconds immediately after the coating, the coated mandrels were placed in static coagulants having the components as set forth in Table 4.1. Porous polyurethane tubings 3WEA1010-0510, 3WEA1082-0510, 3WEA1064-0510, 3WEA3010-0510, 3WEA3064-0510, 3WEA5010-0510 and 3WEA5064-0510 were prepared by following the procedures of the invention and the conditions as indicated in Table 4.1.

Certain physical properties of these prepared tubings are summarized in Table 4.2. As it can be seen from Table 4.2 that when water/ethanol/DMF solutions are used as coagulants, and W is increased from 10 to 50, if ESF and ASF are controlled at an appropriate value, the resultant porous polyurethane tubings have uniform porous structure. It can also be seen from Table 4.2 that the porous polyurethane tubings all have a burst pressure larger than 2100 mm Hg, a pore size from 1–26 μm and an area pososity of 25–42%. The cytotoxicity and hemolytic indexes as set forth in Table 4.2 indicate that the porous polyurethane tubings of this example show no cytotoxicity response or hemolytic phenomenon.

TABLE 4.1

| Coagulant No. | | WEA1010 | WEA1082 | WEA1064 | WEA3010 | WEA3064 | WEA5010 | WEA5064 |
|---|---|---|---|---|---|---|---|---|
| Composition parameters of coagulants | W [1] | 10 | 10 | 10 | 30 | 30 | 50 | 50 |
| | S = 100-W [2] | 90 | 90 | 90 | 70 | 70 | 50 | 50 |
| | ESF [3] | 1.0 | 0.8 | 0.6 | 1.0 | 0.6 | 1.0 | 0.6 |
| | ASF [4] | 0.0 | 0.2 | 0.4 | 0.0 | 0.4 | 0.0 | 0.4 |
| Temperature of Cougulant (°C.) | | 25 ± 2 | 25 ± 2 | 25 ± 2 | 25 ± 2 | 25 ± 2 | 25 ± 2 | 25 ± 2 |
| Coagulating Time (hour) | | 10 | 10 | 10 | 12 | 12 | 12 | 12 |
| Composition of Swelling Agent (Water/Ethanol, wt/wt %) | | 10/90 | 10/90 | 10/90 | 10/90 | 10/90 | 10/90 | 10/90 |
| Temperature of Swelling Agent (°C.) | | 20 ± 2 | 20 ± 2 | 20 ± 2 | 20 ± 2 | 20 ± 2 | 20 ± 2 | 20 ± 2 |
| Swelling Time (min) | | 10 | 10 | 10 | 10 | 10 | 10 | 10 |
| Composition of Rinsing Solution (Water/ethanol, wt/wt %) | | 20/80 | 20/80 | 20/80 | 20/80 | 20/80 | 20/80 | 20/80 |
| Rinsing Time (min) | | 30 | 30 | 30 | 30 | 30 | 30 | 30 |
| Drying Temperature (°C.) | | 40 ± 2 | 40 ± 2 | 40 ± 2 | 40 ± 2 | 40 ± 2 | 40 ± 2 | 40 ± 2 |
| Porous PU Tubing No. | | 3WEA1010-0510 | 3WEA1082-0510 | 3WEA1064-osto | 3WEA3010-0510 | 3WEA3064-0510 | 3WEA5010-0510 | 3WEA5064-0510 |

TABLE 4.2

| PU Tubing Characteristics | Porous PU Tubing | | | | | | |
|---|---|---|---|---|---|---|---|
| | 3WEA 1010-5010 | 3WEA 1082-0510 | 3WEA 1064-0510 | 3WEA 3010-0510 | 3WEA 3064-0510 | 3WEA 5010-0510 | 3WEA 5064-0510 |
| Internal Diameter (mm) | 5.1 ± 0.2 | 5.1 ± 0.2 | 5.1 ± 0.2 | 5.2 ± 0.2 | 5.2 ± 0.2 | 5.3 ± 0.2 | 5.3 ± 0.2 |
| Wall Thickness (mm) | 1.05 ± 0.05 | 1.05 ± 0.05 | 1.05 ± 0.05 | 1.05 ± 0.05 | 1.05 ± 0.05 | 1.05 ± 0.05 | 1.05 ± 0.05 |
| Pore Homogeneity [1] | homogenous | homogenous | homogenous | homogenous | homogenous | homogenous | homogenous |
| Burst Pressure (mmHg) | 2150 ± 76 | 2200 ± 76 | 2250 ± 76 | — | — | 2100 ± 70 | 2180 ± 76 |
| ASTM F895 Cytoxicity | 0/0 | 0/0 | 0/0 | 0/0 | 0/0 | 0/0 | 0/0 |
| ASTM F756 Hemolytic Index (%) | ○ | ○ | ○ | ○ | ○ | ○ | ○ |
| Pore size μm [1] | 1–15 | 2–10 | 2–12 | 4–16 | 5–19 | 5–23 | 4–26 |
| Area Porosity %, [2] | 25 | 28 | 33 | 39 | — | 42 | 39 |

Note:
(1) Pore size is determined by measuring the pore image taken by SEM in the cross-section of the wall of the porous polyurethane tubing specimen by using a computer image analysis technique.
(2) Area porosity = sum of pore area in a unit image areaunit image area?

The pore area and unit area are determined by calculating a unit image taken by SEM in the cross-section of the wall of the porous polyurethane tubing by using computer image analysis system.

Example 5

Polyurethane resins Nos. 4,5,6,7,8,9, and 10 of Table 1 were coated over the outer surfaces of cylindrical metal mandrels having an outer diameter of 6 mm and a coating thickness of 0.8 mm. Within 30 seconds immediately after the coating, the coated mandrels were placed in static coagulants having the components as set forth in Table 5.1. Porous polyurethane tubings 4WEA15955-0508, 5WEA15955-0508, 6WEA15955-0508, 7WEA15955-0508, 8WEA15955-0508, 9WEA15955-0508 and 10WEA15955-0508 were prepared by following the procedures of the invention and the conditions as indicated in Table 5.1.

Certain physical properties of these prepared tubings are summarized in Table 5.2. As it can be seen from Table 5.2 that when water/ethanol/DMF solutions are used as coagulants, and W is controlled at 15%, ESF is 0.95 and ASF is controlled at 0.05, the resultant porous polyurethane is controlled at 0.05, the resultant porous polyurethane tubings have uniform porous structure. It can also be seen from Table 5.2 that the porous polyurethane tubings all have a high burst pressure, a pore size from 2–32 μm and an area pososity of 17–40%. The cytotoxicity and hemolytic indexes as set forth in Table 5.2 indicate that the porous polyurethane tubings of this example show no cytotoxicity response or hemolytic phenomenon.

TABLE 5.1

| Coagulant No. | | WEA15955 | WEA15955 | WEA15955 | WEA15955 | WEA16965 | WEA15955 | WEA15955 |
|---|---|---|---|---|---|---|---|---|
| Compostion Parameters of Coagulants | W [1] | 15 | 15 | 15 | 15 | 15 | 15 | 15 |
| | S = 100-W [2] | 85 | 85 | 85 | 85 | 85 | 85 | 85 |
| | ESF [3] | 0.95 | 0.95 | 0.95 | 0.95 | 0.95 | 0.95 | 0.95 |
| | ASF [4] | 0.05 | 0.05 | 0.05 | 0.05 | 0.05 | 0.05 | 0.05 |
| PU Resin No. | | 4 | 5 | 6 | 7 | 8 | 9 | 10 |
| Temperature of Coagulant (°C.) | | 30 ± 2 | 30 ± 2 | 30 ± 2 | 30 ± 2 | 30 ± 2 | 30 ± 2 | 30 ± 2 |
| Coagulating Time (hour) | | 6 | 6 | 6 | 6 | 6 | 6 | 6 |
| Composition of Swelling Agent (Water/Ethanol, wt/wt %) | | 10/90 | 10/90 | 10/90 | 10/90 | 10/90 | 10/90 | 10/90 |
| Temperature of Swelling Agent (°C.) | | 25 ± 2 | 25 ± 2 | 25 ± 2 | 25 ± 2 | 25 ± 2 | 25 ± 2 | 25 ± 2 |
| Swelling Time (min) | | 50 | 50 | 50 | 50 | 50 | 50 | 50 |
| Composition of Rinsing Solution (Water/Ethanol, wt/wt %) | | 20/80 | 20/80 | 20/80 | 20/80 | 20/80 | 20/80 | 20/80 |
| Rinsing Time (min) | | 120 | 120 | 120 | 120 | 120 | 120 | 120 |
| Drying Temperature (°C.) | | 40 ± 2 | 40 ± 2 | 40 ± 2 | 40 ± 2 | 40 ± 2 | 40 ± 2 | 40 ± 2 |
| Porous PU Tubing No. | | 4WEA15955-0508 | 5WEA15955-0508 | 6WEA15955-0508 | 7WEA15955-0508 | 8WEA15955-0508 | 9WEA15955-0508 | 10WEA15955-0508 |

TABLE 5.2

| PU Tubing Characteristics | Pourous PU tubing | | | | | | |
|---|---|---|---|---|---|---|---|
| | 4WEA15955-0508 | 5WEA15955-0508 | 6WEA15955-0508 | 7WEA15955-0508 | 8WEA15955-0508 | 9WEA15955-0508 | 10WEA15955-0508 |
| Internal Diameter (mm) | 5.2 ± 0.2 | 5.2 ± 0.2 | 5.2 ± 0.2 | 5.2 ± 0.2 | 5.2 ± 0.2 | 5.2 ± 0.2 | 5.2 ± 0.2 |
| Wall Thickness (mm) | 0.76 ± 0.05 | 0.76 ± 0.05 | 0.76 ± 0.05 | 0.76 ± 0.05 | 0.76 ± 0.05 | 0.76 ± 0.05 | 0.76 ± 0.05 |
| Pore Homogeneity | homogenous | homogenous | homogenous | homogenous | homogenous | homogenous | homogenous |

TABLE 5.2-continued

| PU Tubing Characteristics | Pourous PU tubing | | | | | | |
|---|---|---|---|---|---|---|---|
| | 4WEA15955-0508 | 5WEA15955-0508 | 6WEA15955-0508 | 7WEA15955-0508 | 8WEA15955-0508 | 9WEA15955-0508 | 10WEA15955-0508 |
| Burst Pressure (mmHg) | 1950 ± 76 | 1880 ± 76 | 1800 ± 76 | 2450 ± 76 | 1960 ± 76 | — | — |
| ASTM F895 Cytotoxicity | 0/0 | 0/0 | 0/0 | 0/0 | 0/0 | 0/0 | 0/0 |
| ASTM F756 Hemolytic Index (%) | ○ | ○ | ○ | ○ | ○ | ○ | ○ |
| Pore Size μm [1] | 5–15 | 4–20 | 4–30 | 2–13 | 2–18 | 2–32 | 2–18 |
| Area Porosity % [2] | 30 | 32 | 33 | 17 | 33 | 40 | 34 |

Example 6

Polyurethane resins Nos. 11–16 of Table 1 were coated over the outer surfaces of cylindrical metal mandrels having an outer diameter of 4 mm and a coating thickness of 0.4 mm. Within 30 seconds immediately after the coating, the coated mandrels were placed in static coagulants having the components as set forth in Table 6.1. Porous polyurethane tubings 11WEA208515-0304, 12WEA208515-0304, 13WEA208515-0304, 14WEA208515-0304, 15WEA208515-0304, and 16WEA208515-0304 were prepared by following the procedures of the invention and the conditions as indicated in Table 6.1.

Certain physical properties of these prepared tubings are summarized in Table 6.2. As it can be seen from Table 6.2 that when water/ethanol/DMF solutions are used as coagulants, and W is controlled at 20%, ESF is 0.85 and ASF is controlled at 0.15, the resultant porous polyurethane tubings have uniform porous structure. It can also be seen from Table 6.2 that the porous polyurethane tubings have a pore size from 2–23 μm and an area pososity of 23–31%. The cytotoxicity and hemolytic indexes as set forth in Table 6.2 indicate that the porous polyurethane tubings of this example show no cytotoxicity response or hemolytic phenomenon.

TABLE 6.1

| Coagulant No. | | WEA 208515 | WEA 208515 | WEA 208515 | WEA 208515 | WEA 208515 | WEA 208515 |
|---|---|---|---|---|---|---|---|
| Composition | W | 20 | 20 | 20 | 20 | 20 | 20 |
| Parameters of | S = 100-W | 80 | 80 | 80 | 80 | 80 | 80 |
| Coagulants | ESF | 0.85 | 0.85 | 0.85 | 0.85 | 0.85 | 0.85 |
| | ASF | 0.15 | 0.15 | 0.15 | 0.15 | 0.15 | 0.15 |
| PU Resin No. | | 11 | 12 | 13 | 14 | 15 | 16 |
| Temperature of Coagulant (°C.) | | 25 ± 2 | 25 ± 2 | 25 ± 2 | 25 ± 2 | 25 ± 2 | 25 ± 2 |
| Coagulating Time (hour) | | 8 | 8 | 8 | 8 | 8 | 8 |
| Composition of Swelling Agent (Water/Ethanol, wt/wt %) | | 5/95 | 5/95 | 5/95 | 5/95 | 5/95 | 5/95 |
| Temperature of Swelling Agent (°C.) | | 25 ± 2 | 25 ± 2 | 25 ± 2 | 25 ± 2 | 25 ± 2 | 25 ± 2 |
| Swelling Time (min) | | 30 | 30 | 30 | 30 | 30 | 30 |
| Composition of Rinsing Solution (Water/Ethanol, wt/wt %) | | 15/85 | 15/85 | 15/85 | 15/85 | 15/85 | 15/85 |
| Rinsig Time (min) | | 60 | 60 | 60 | 60 | 60 | 60 |
| Drying Temperature (°C.) | | 40 ± 2 | 40 ± 2 | 40 ± 2 | 40 ± 2 | 40 ± 2 | 40 ± 2 |
| Porous PU Tubing No. | | 11WEA208515-0304 | 12WEA208515-0304 | 13WEA208515-0304 | 14WEA208515-0304 | 15WEA208515-0304 | 16WEA208515-0304 |

TABLE 6.2

| PU Tubing Characteristics | Porous PU tubing | | | | | |
|---|---|---|---|---|---|---|
| | 11WEA2085 15-0304 | 12WEA2085 15-0304 | 13WEA2085 15-0304 | 14WEA2085 15-0304 | 15WEA2085 15-0304 | 16WEA2085 15-0304 |
| Internal Diameter (mm) | 3.2 ± 0.2 | 3.2 ± 0.2 | 3.2 ± 0.2 | 3.2 ± 0.2 | 3.2 ± 0.2 | 3.2 ± 0.2 |
| Wall Thickness (mm) | 0.37 ± 0.05 | 0.37 ± 0.05 | 0.36 ± 0.05 | 0.36 ± 0.05 | 0.37 ± 0.05 | 0.37 ± 0.05 |
| Pore Homogeneity | homogenous | homogenous | homogenous | homogenous | homogenous | homogenous |
| ASTM F895 Cytotoxicity | 0/0 | 0/0 | 0/0 | 0/0 | 0/0 | 0/0 |
| ASTM F756 Hemolytic Index | O | O | O | O | O | O |
| Pore Size μm | 2–10 | 2–14 | 2–20 | 2–23 | 2–18 | 2–20 |
| Area Porosity % | 28 | 30 | 31 | 29 | 24 | 23 |

Example 7

In this example, several porous polyurethane tubings prepared in the previous examples were implanted in dogs for a chronic animal test to survey the biocompatibility. The survey method and results are summarized in Table 7 below.

TABLE 7

| Animal Nos. | implanted position | PU tubing implanted |
|---|---|---|
| dog (#1) (25 Kg) results: | iliac artery of left leg | 1WA5050-0705 I.D. (7.5 mm) | no blocking, taken out and checked by observation, 2 years after the implantation

| dog (#2) (20 Kg) results: | iliac artery of left leg | 1WA5050-0705 I.D. (7.5 mm) | no blocking, taken out and checked by observation, 2 years after the implantation

| dog (#3) (25 Kg) results: | femoral artery | 5WEA15955-0508 I.D. (5.2 mm) | no blocking, checked by angiography, 2 years after the implantation

| dog (#4) (20 Kg) results: | right femoral artery | PU tubing prepared by using PU resin No. 2 and coagulant WA5050, I.D. (3 mm) | no blocking, checked by angiography, 2 years after the implantation

| dog (#4) (20 Kg) results: | left femoral artery | PU tubing prepared by using PU resin No. 2 and coagulant WA5050, I.D. (3 mm) | no blocking, checked by angiography, 2 years after the implantation

| dog (#5) (20 Kg) results: | right femoral artery | PU tubing prepared by using PU resin No. 2 and coagulant WA5050, I.D. (3 mm) | no blocking, checked by angiography, 2 years after the implantation

| dog (#5) (20 Kg) results: | left femoral artery | PU tubing prepared by using PU resin No. 2 and coagulant WA5050, I.D. (3 mm) | no blocking, checked by antjiography, 2 years after the implantation

| dog (#6) | right femoral artery | PU tubing prepared |

TABLE 7-continued

| Animal Nos. | implanted position | PU tubing implanted |
|---|---|---|
| (20 Kg) results: | | by using PU resin No. 5 and coagulant WEA15955, I.D. (3 mm) | no blocking, checked by angiography, 1.5 years after the implantation

| dog (#6) (20 Kg) results: | left femoral artery | PU tubing prepared by using PU resin No. 5 and coagulant WEA15955, I.D. (3 mm) | no blocking, checked by angiography, 1.5 years after the implantation

It can be seen from the above illustrative examples and tables that the porous polyurethane tubings fabricated by the method of the invention have homogeneous pore structure and superior blood compatibility and therefore are suitable for being used as vascular graft prostheses.

What is claimed is:

1. A method of preparing porous polyurethane vascular graft, comprising the following steps:

(a) coating a solvent type polyurethane resin on the outer surface of a cylindrical mandrel, said polyurethane resin being prepared from polytetramethylene glycol, glycols and 4,4'-diphenylmethane diisocyanate, and having a solid content of 15–45 percent by weight and a viscosity of 10,000 to 150,000 centipoises;

(b) within 30 seconds after the coating step (a) placing the coated mandrel in a static coagulant having a temperature of 15°–40° C. for 2 to 12 hours to form a porous polyurethane tubing surrounding the mandrel, said coagulant consisting of water, ethanol and, optionally, an aprotic solvent;

(c) placing the mandrel surrounded with the porous polyurethane tubing in a swelling agent for 5 to 60 minutes, said swelling agent containing at least 90 percent by weight ethanol;

(d) separating the porous polyurethane tubing from the mandrel;

(e) rinsing the porous polyurethane tubing with a solution containing at least 80 percent by weight ethanol for 5 to 120 minutes; and (f) drying the porous polyurethane tubing to obtain a porous polyurethane vascular graft with an area porosity of 15°–50% and a pore size of 1 to 30 μm.

2. The method as claimed in claim 1, in which the polytetramethylene glycol has a molecular weight of 1000 to

2000.

3. The method as claimed in claim 1, in which the glycol is selected from the group consisting of ethylene glycol, 1,4-butylene glycol and 1,6-hexamethylene glycol.

4. The method as claimed in claim 3, wherein the glycol is 1,4-butylene glycol.

5. The method as claimed in claim 1, wherein the solvent type polyurethane resin is prepared from 1 mole of polytetramethylene glycol, 0.8 to 4.0 mole of glycol and 1.8 to 5.0 mole of 4,4'-diphenylmethane diisocyanate.

6. The method as claimed in claim 1, wherein the aprotic solvent is N,N-dimethyl acetamide.

7. The method as claimed in claim 1, wherein the aprotic solvent is N,N,-dimethyl formamide.

8. The method as claimed in claim 1, wherein the coagulant consists of from 10 to 50 percent by weight of water and from 90 to 50 percent by weight of a solvent, said solvent being ethanol or an aprotic solvent, wherein the weight fraction of the ethanol is from 1.0 to 0.4 and the weight fraction of aprotic solvent is 0 to 0.6

9. The method as claimed in claim 1, wherein in step (a) the solvent type polyurethane resin is coated over the mandrel to a thickness of 0.3 mm to 1.0 mm, and the resulting porous vascular graft has a wall thickness of 0.25 mm to 0.9 mm.

10. The method as claimed in claim 1, wherein the mandrel is metal and has an outer diameter of 2 mm to 15 mm.

11. The method as claimed in claim 1, wherein in step (a), the coating of solvent type polyurethane resin is conducted at a temperature of 10° to 40° C.

12. The method as claimed in claim 1, wherein the aprotic solvent is selected from the group consisting of N,N-dimethyl formamide and N,N-dimethyl acetamide.

\* \* \* \* \*